United States Patent [19]

Igarashi et al.

[11] 4,201,774

[45] May 6, 1980

[54] NOVEL AMINOGLYCOSIDE DERIVATIVES

[75] Inventors: Kikuo Igarashi, Itami; Tamio Sugawara, Mino, both of Japan

[73] Assignee: Shionogi & Co., Ltd., Osaka, Japan

[21] Appl. No.: 960,559

[22] Filed: Nov. 14, 1978

[30] Foreign Application Priority Data

Dec. 29, 1977 [JP] Japan .................................. 52-158496

[51] Int. Cl.$^2$ ........................ A61K 31/71; C07H 15/24
[52] U.S. Cl. ....................................... 424/180; 536/10; 536/17 R
[58] Field of Search ....................... 536/17, 10; 424/180

[56] References Cited

U.S. PATENT DOCUMENTS

| | | | |
|---|---|---|---|
| 3,282,783 | 11/1966 | Vanderhaeghe | 536/17 |
| 3,925,353 | 12/1975 | Umezawa et al. | 536/17 |
| 4,002,742 | 1/1977 | Wright et al. | 536/17 |
| 4,117,221 | 9/1978 | Daniels | 536/17 |

*Primary Examiner*—Johnnie R. Brown
*Attorney, Agent, or Firm*—Wenderoth, Lind & Ponack

[57] ABSTRACT

Novel aminoglycoside derivatives and their salts, of which the 1-amino group is modified with groups represented by the formula:

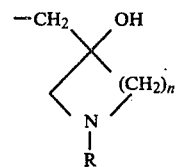

(wherein R is hydrogen, lower alkyl, or aralkyl; and n is an integer of 1 to 3.) effective in treatment and prevention of infectious diseases caused by gram-positive and gram-negative bacteria.

9 Claims, No Drawings

NOVEL AMINOGLYCOSIDE DERIVATIVES

I. Background of the Invention

Aminoglycoside antibiotics, for example, streptomycin, kanamycins, gentamicins, tobramycin, etc. have practically been used as broad spectrum antimicrobials effective against gram-positive, gram-negative, and acid-fast bacteria. The aminoglycoside antibiotics, however, are sometimes accompanied by undesired side effects such as nephropathy and deafness. Occurrence of resistant strains against the aminoglucosides is another problem to be solved. It has been attempted to modify such aminoglycosides with specified groups at the 1-amino group in order to improve the antimicrobial activity and relatively decrease the side effects.

The present inventors have found that the antimicrobial spectrum and potency of activity are improved by acylation of the 1-amino group with α-hydroxy-α-heterocycleacetic acids, followed by reduction of the carbonyl group. The present invention is based upon this finding.

the dotted line represents the presence or absence of a double bond.)

The aminoglycosides (I) used as starting materials in this invention containing 2-deoxystreptamine moiety are represented by the formula:

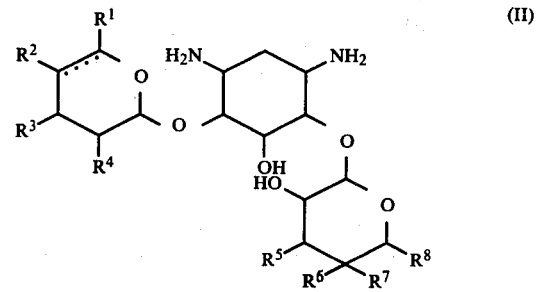

(wherein $R^1$, $R^2$, $R^3$, $R^4$, $R^5$, $R^6$, $R^7$, $R^8$, and the dotted line each has the same meaning as mentioned above.)

Representative of the compounds (II) and their substituents are shown in Table 1.

Table 1

| Generic Name | $R^1$ | $R^2$ | $R^3$ | $R^4$ | $R^5$ | $R^6$ | $R^7$ | $R^8$ | dotted line |
|---|---|---|---|---|---|---|---|---|---|
| tobramycin | $CH_2NH_2$ | OH | H | $NH_2$ | $NH_2$ | H | OH | $CH_2OH$ | none |
| kanamycin A | " | " | OH | OH | – | " | " | " | " |
| kanamycin B | " | " | " | $NH_2$ | " | " | " | " | " |
| kanamycin C | $CH_2OH$ | " | " | " | " | " | " | " | " |
| deoxykanamycin A | $CH_2NH_2$ | " | H | OH | " | " | " | " | " |
| dideoxykanamycin B (dibekacin) | " | H | " | $NH_2$ | " | " | " | " | " |
| gentamicin $C_1$ | $CH(CH_3)NHCH_3$ | " | " | " | $NHCH_3$ | OH | $CH_3$ | H | " |
| gentamicin $C_2$ | $CH(CH_3)NH_2$ | " | " | " | " | " | " | " | " |
| gentamicin $C_{1a}$ | $CH_2NH_2$ | " | " | " | " | " | " | " | " |
| gentamicin B | " | " | OH | OH | " | " | " | " | " |
| sisomicin | " | " | H | $NH_2$ | " | " | " | " | double bond |

II. Summary of the Invention

This invention relates to novel aminoglycoside derivatives having an excellent antimicrobial action. More particularly, this invention relates to novel aminoglycoside antibiotic derivatives represented by the following formula and their salts.

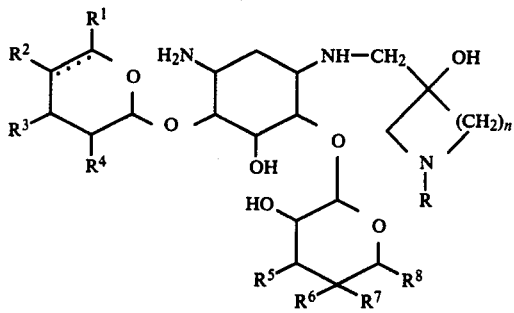

(wherein
R is hydrogen, lower alkyl or aralkyl;
$R^1$ is aminomethyl, hydroxymethyl, 1-aminoethyl, or 1-methylaminoethyl;
$R^2$, $R^3$, and $R^6$ each is hydrogen or hydroxy;
$R^4$ is hydroxy or amino;
$R^5$ is amino or methylamino;
$R^7$ is hydroxy or methyl;
$R^8$ is hydrogen or hydroxymethyl;
n is an integer of 1 to 3; and

III. Detailed Explanation

In the aforementioned general formula (I), the lower alkyls as R mean $C_1$ to $C_5$ alkyls, for example, methyl, ethyl, propyl, isopropyl, butyl, isobutyl, s-butyl, t-butyl, pentyl, isopentyl, neopentyl, t-pentyl, and the like. The aralkyls include benzyl, phenethyl, phenylpropyl, and the like.

The novel aminoglycoside antibiotic derivatives (I) in this invention include the free bases and salts thereof, particularly non-toxic acid addition salts, for example, salts with inorganic acids such as hydrochloric acid, hydrobromic acid, hydroiodic acid, sulfuric acid, phosphoric acid, carbonic acid, and the like and salts with organic acids such as acetic acid, fumaric acid, malic acid, tartaric acid, maleic acid, citric acid, mandelic acid, ascorbic acid, gallic acid, and the like.

Representative of the compounds (I) are:
(1) 1-N-[(3-hydroxyazetidin-3-yl)methyl]tobramycin
(2) 1-N-[(3-hydroxypyrrolidin-3-yl)methyl]tobramycin
(3) 1-N-[(3-hydroxypiperidin-3-yl)methyl]tobramycin
(4) 1-N-[(3-hydroxyazetidin-3-yl)methyl]kanamycin A
(5) 1-N-[(3-hydroxypyrrolidin-3-yl)methyl]kanamycin A
(6) 1-N-[(3-hydroxypiperidin-3-yl)methyl]kanamycin A

IV. Preparation

Compounds (I) may readily be prepared by reduction of the 1-amino acylated aminoglycosides represented by the formula:

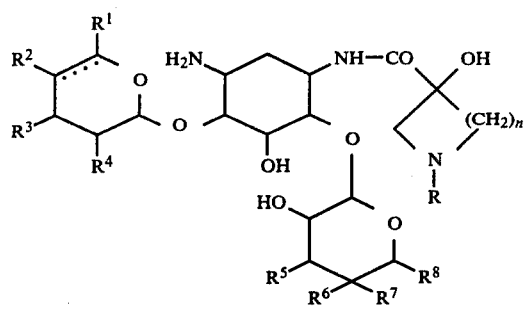

(III)

(wherein R, $R^1$, $R^2$, $R^3$, $R^4$, $R^5$, $R^6$, $R^7$, $R^8$, n, and the dotted line each has the same meaning as mentioned above.) Compounds (III) as starting materials are described in Japanese Unexamined Patent Application Nos. 51-130119, 52-112840, and 52-114176. For example, one of the starting materials represented by the formula:

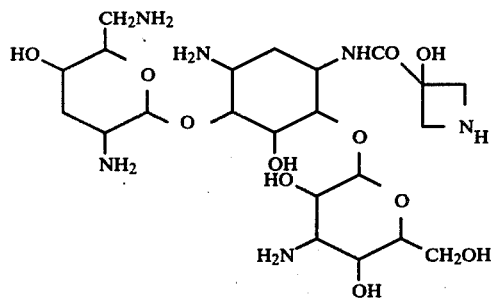

(IIIa)

may be prepared by acylation of tobramycin with N-hydroxysuccinimido ester of 3-hydroxyazetidine-3-carboxylic acid, during which reaction the functional groups other than the 1-amino group are properly protected and deprotected after termination of the acylation.

Representative reducing agents are diborane, lithium aluminium hydride, lithium aluminium hydride-aluminium chloride, sodium borohydride-aluminium chloride, sodium borohydride-boron trifluoride etherate, and the like reducing agents which may usually be employed in selective reduction of the amide.

The reduction may be effected in a suitable anhydrous solvent. In carrying out the reaction, an equimolar amount of excess amount of reducing agent, preferably about 1 to 2 equivalents, may be used to 1 mole of the starting aminoglycosides (III). This reaction proceeds well even at room temperature, but if required, it may be accelerated by carrying out under refluxing of the reaction medium. Preferably, this reaction is conducted under innert gas, more preferably under nitrogen atmosphere. Representative solvents are ethers such as diethyl ether, dioxane, tetrahydrofuran, monoglyme, and diglyme, and they may be employed alone or as a mixture of two or more kinds of them. The reaction usually terminates within a period of several hours, practically 1 to 8 hours.

It is preferred that the starting materials (III) are employed in a form of acid additional salts with strong acids such as trifluoroacetic acid because the salts are soluble in the solvents.

V. Effect

The aminoglycoside antibiotic derivatives (I) and the non-toxic salts thereof prepared in this invention exhibit excellent antimicrobial activities. They are several to several ten times more active than the corresponding well-known aminoglycosides against gram-positive and gram-negative bacteria. The minimum inhibitory concentration (MIC, μg/ml) of the compounds of this invention and that of the corresponding well-known aminoglycosides are indicated comparatively in Table 2.

Table 2

MIC of TOB derivatives, KM-A derivatives and TOB

| Bacteria | (1) | (2) | (3) | (4) | (5) |
|---|---|---|---|---|---|
| Staphylococcus aureus S-25* | 50 | 25 | 25 | 12.5 | 100 |
| Staphylococus epidermidis TB-302 | 3.13 | 1.56 | 3.13 | 1.56 | 3.13 |
| Escherichia coli EC-147* | 3.13 | 3.13 | 6.25 | 6.25 | 50 |
| Escherichia coli EC-148* | 3.13 | 3.13 | 12.5 | 6.25 | 100 |
| Escherichia coli W-677/JR 214* | 1.56 | 1.56 | 6.25 | 3.13 | 100 |
| Escherichia coli W-677/JR 225* | 1.56 | 0.78 | 3.13 | 3.13 | 50 |
| Escherichia coli W-677/JR-762* | 3.13 | 3.13 | 12.5 | 12.5 | >100 |
| Klebsiella pneumoniae Kl-187* | 0.78 | 0.39 | 1.56 | 1.56 | 25 |
| Enterobacter cloacae Cl-126* | 0.78 | 0.78 | 1.56 | 1.56 | 25 |
| Citrobactor freundii Ct-52* | 0.78 | 0.78 | 3.13 | 1.56 | 25 |
| Seratia marcescens MA-81* | 12.5 | 12.5 | 12.5 | 12.5 | >100 |
| Proteus mirabilis TB-617* | 1.56 | 1.56 | 6.25 | 3.13 | 6.25 |
| Proteus inconstans In-43* | 6.25 | 12.5 | 3.13 | 3.13 | 6.25 |
| Pseudomonas aeruginosa PP-6* | 0.78 | 0.78 | 3.13 | 3.13 | 50 |
| Pseudomonas aeruginosa TB-485* | 6.25 | 3.13 | 6.25 | 6.25 | 25 |

(Note)
(1) = 1-N-[(3-hydroxyazetidin-3-yl)methyl]tobramycin
(2) = 1-N-[(3-hydroxypyrrolidin-3-yl)methyl]tobramycin
(3) = 1-N-[(3-hydroxyazetidin-3-yl)methyl]kanamycin A
(4) = 1-N-[(3-hydroxypyrrolidin-3-yl)methyl]kanamycin A
(5) = tobramycin
* = tobramycin resistant strains As shown in Table 2, the compounds (I) of this invention are valuable antimicrobial agents effective against various species of gram-positive and gram-negative bacteria, and useful as drugs used for humans and other kinds of animals. They can be used in prevention or treatment of infectious diseases caused by aminoglycoside sensitive strains as well as resistant strains (e.g. Escherichia coli, Klebsiella pneumoniae, Proteus mirabilis, Pseudomonas aeruginosa).

The compounds (I) of this invention can also be used as disinfectants for preventing the growth of bacteria alive in perishables, feedstuffs or hygenical materials.

VI. How to use

The compounds (I) of this invention can be used in a wide variety of oral or parenteral dosage forms solely or by admixture with other co-acting substances. The pharmaceutical compositions may be a mixture of 0.01 to 99% of the compounds (I) with a pharmaceutical carrier or carriers which can be solid material or liquid material, in which the compounds (I) are soluble, dispersible or suspensible. They can be in a unit dosage form. The solid compositions can be in forms of tablets, powder, dry syrups, troches, granules, capsules, pills, suppositories or like solid preparations. The liquid compositions can be in forms of injection, ointment, dispersion, inhalant, suspension, solution, emulsion, syrup or elixir. All of diluents (e.g. starch, sucrose, lactose, calcium carbonate, kaolin), bulking agents (e.g. lactose, sugar, salt, glycine, starch, calcium carbonate, calcium phosphate, kaolin, bentonite, talc, sorbitol), binders (e.g. starch, acacia, gelatin, glucose, sodium arginate, tragacanth, carboxymethylcellulose, sorbitol, polyvinylpyrrolidone), disintegrators (e.g. starch, agar, carbonate, sodium laurylsulfate), lubricants (e.g. stearic acid, talc, paraffin, boric acid, silica, sodium benzoate, polyethyleneglycol, cacao oil, magnesium sulfate), emulsifying agents (e.g. lecithin, sorbitan monooleate, acacia), suspending agents (e.g. sorbitol, methylcellulose, glucose, sugar syrup, gelatin, hydroxyethylcellulose, carboxymethylcellulose, aluminium stearate gel, hydrogenated fats), solvents (e.g. water, peanut oil, sesame oil, methyl oleate), preservatives (e.g. methyl or ethyl p-hydroxybenzoate, sorbic acid), edible coloring agents, aromatic substances, solubilizing agents, buffers, stabilizing agents, dispersing agents, wetting agents, antioxidants, and the like can be used in the conventional manners as far as they do not act adversely on the compounds (I).

The compounds (I) of this invention, particularly their sulfates, are readily soluble in water and conveniently used as a solution for intravenous, intramuscular or subcutaneous injection according to a conventional method. The compound (I) can be dissolved in an aqueous or oily solvent for injection to give an injectable solution in an ampoule, in order to preserve the injectable preparation for a long period of time, it is appropriate to make a vial preparation containing crystalline, powder, microcrystalline or lyophilizate of the compound (I). The vial preparation may be dissolved or suspended in the said solvent for injection immediately before use. The preparation may contain the said preservatives.

Further, the compounds (I) of this invention can be used as suppositories, ointments for topical or ophthalmic use, powders for topical use, and like preparations preparable according to the methods well-known to those skilled in the art. The external preparation can contain 0.01 to 99% of the compound (I) of this invention together with a necessary amount of pharmaceutical carrier given above.

This invention also provides a method for treating or preventing infections caused by bacteria in humans or domestic animals, which comprises administering the compounds (I) of this invention to the humans or animals at single or divided doses of 0.01 to 5 g/kg a day for injection, 0.01 to 10 g/kg a day for oral administration or 0.01 to 10 g/kg a day for a local application at intervals of 3 to 12 hours.

The method is applicable for treating or preventing some infectious diseases caused by bacteria sensitive to the compounds of this invention, e.g. staphylodermia, anthropozoonosis, cystitis, pyelitis, pneumonia, pneumonitis, bronchitis, empyematic, naspharyngitis, tonsilitis, rhinitis, dermatitis, pustulosis, abscess, wound and soft tissue infections, ear infections, osteomyelitis, septicemia, enteritis, urinary tract infections, and pyelonephritis.

Preferably, the compounds (I) of this invention are given to a patient in forms of pharmaceutical preparation, e.g. powder, dry syrup, tablet, troch, granule, capsule, pill, suppository, injection, ointment, dispersion, inhalant, suspension, solution, emulsion, syrup, and elixir. They may be in a unit dosage form, e.g. tablet, troch, capsule, injection, vial, granule, or powder in a separate container of package.

The following examples are provided to further illustrate this invention.

EXAMPLE

Preparation of 1-N-[(3-hydroxyazetidin-3-yl)methyl]tobramycin sulfate

1-N-[(3-hydroxyazetidin-3-yl)carbonyl]tobramycin (500 mg) is dissolved in 4 ml of anhydrous trifluoroacetic acid under ice-cooling and the excess amount of trifluoroacetic acid is evaporated under reduced pressure. The resulting vitrified residue is dissolved in 17 ml of dry tetrahydrofuran and 66 ml of a 1 M solution of diborane in tetrahydrofuran is dropwise added thereto over a period of 4 hours under nitrogen atmosphere. The reaction mixture is stirred at 50° C. for 6 hours, cooled, and after decomposition of the excess amount of diborane with a small amount of water, evaporated under reduced pressure. The residue is dissolved in 30 ml of water, adjusted to pH 11 to 12 with an aqueous sodium hydroxide solution, and then adjusted to pH 5 with 10% hydrochloric acid. The solution is adsorbed on a column of 100 ml of Amberlite CG-50 (NH$_4$+ type) and after washing of the column with 200 ml of water, eluted with 1 L of water and 1 L of 1.5 N aqueous ammonium hydroxide solution by a gradient method (one fraction: 12 ml). Fraction Nos. 74 to 79 are combined and evaporated under reduced pressure to yield 229 mg of 1-N-[(3-hydroxyazetidin-3-yl)methyl]tobramycin in 47% yield.

A solution of 140 mg of the above product in 20 ml of water is adjusted to pH 6.0 with about 5 ml of 0.11 N sulfuric acid, concentrated to about 1 to 2 ml under reduced pressure, and treated with 60 ml of ethanol. The resulting precipitate is collected by filtration, washed with ethanol, dissolved in water, treated with active carbon (Norit A), and filtered through a pyrex filter. The filtrate is lyophilized, and the lyophilizate is allowed to stand to absorb the moisture up to stationary state yielding 166 mg of 1-N-[(3-hydroxyazetidin-3-yl)methyl]tobramycin sulfate. $[\alpha]_D^{23.5}$ +62.5±1.0° (c=1.036, H$_2$O)

Elemental Analysis

Calcd(%) for C$_{22}$H$_{44}$N$_6$O$_{10}$.2.3H$_2$SO$_4$.7.5H$_2$O: C,28.43; H,6.90; N,9.04; S,7.94. Found(%): C,28.43; H,6.62; N, 8.97; S,7.86.

NMR: $\delta_{ppm}^{D_2O}$ 6.30(d, J=4 Hz), 5.68(d, J=3.5 Hz).

Compounds indicated in Table 3 may be prepared in the same manner.

Table 3

| Ex. No. | Compounds | Yield (%) | Optical Rotation | Elemental Analysis | NMR: $\delta^{D_2O}$ |
|---|---|---|---|---|---|
| 2 | 1-N-[(3-hydroxypyrrolidin-3-yl)methyl]tobramycin sulfate | 45 | $[\alpha]_D^{23.5} = +61.2 \pm 1.0°$ (c = 1.017, H$_2$O) | ($C_{23}H_{46}N_6O_{10}$ . 2.3H$_2$SO$_4$ . 9.5H$_2$O) Calcd (%): C,28.67; H,7.28; N, 8.72; S,7.66. Found (%): C,28.85; H,6.98; N, 8.75; S,7.41 | 6.36(d, J = 3.5Hz), 5.68(d, J = 3Hz) |
| 3 | 1-N-[(3-hydroxyazetidin-3-yl)methyl]kanamycin A sulfate | 39 | $[\alpha]_D^{24.0} = +59.9 \pm 1.0°$ (c = 1.000, H$_2$O) | ($C_{22}H_{43}N_5O_{12}$ . 2H$_2$SO$_4$ . 9H$_2$O) Calcd(%): C,28.47; H,6.84; N, 7.55; S,6.91. Found(%): C,28.25; H, 6.62; N, 7.41; S,7.21. | 6.15(d, J = 3.5Hz), 5.70(d, J = 3Hz). |
| 4 | 1-N-[(3-hydroxypyrrolidin-3-yl)methyl]kanamycin A sulfate | 39 | $[\alpha]_D^{24.0} = +54.0 \pm 0.9°$ (c = 1.010, H$_2$O | ($C_{23}H_{45}N_5O_{12}$ . 2H$_2$SO$_4$ . 10H$_2$O) Calcd (%): C,28.78; H,7.25; N, 7.30; S,6.68. Found(%): C,28.49; H,6.95; N, 7.17; S,6.92. | 6.13(d, J = 3.5Hz), 5.73 (d, J = 3Hz) |

We claim:

1. An aminoglycoside derivative represented by the formula:

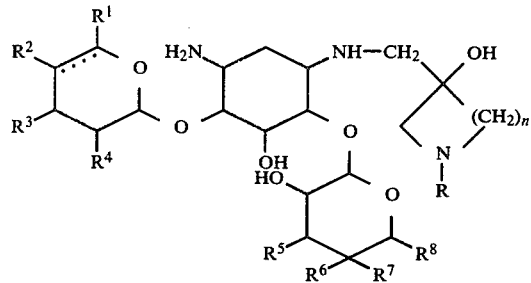

wherein R is hydrogen, lower alkyl, benzyl, phenethyl or phenylpropyl;
$R^1$ is aminomethyl, hydroxymethyl, 1-aminoethyl or 1-methylaminoethyl;
$R^2$, $R^3$, and $R^6$ each is hydrogen or hydroxy;
$R^4$ is hydroxy or amino;
$R^5$ is amino or methylamino;
$R^7$ is hydroxy or methyl;
$R^8$ is hydrogen or hydroxymethyl;
n is an integer of 1 to 3; and
the dotted line represents the presence or absence of a double bond
and the pharmaceutically acceptable acid addition salts thereof.

2. A compound claimed in claim 1, namely 1-N-[(3-hydroxyazetidin-3-yl)methyl]tobramycin.

3. A compound claimed in claim 1, namely 1-N-[(3-hydroxypyrrolidin-3-yl)methyl]tobramycin.

4. A compound claimed in claim 1, namely 1-N-[(3-hydroxypiperidin-3-yl)methyl]tobramycin.

5. A compound claimed in claim 1, namely 1-N-[(3-hydroxyazetidin-3-yl)methyl]kanamycin A.

6. A compound claimed in claim 1, namely 1-N-[(3-hydroxypyrrolidin-3-yl)methyl]kanamycin A.

7. A compound claimed in claim 1, namely 1-N-[(3-hydroxypiperidin-3-yl)methyl]kanamycin A.

8. A composition comprising an effective amount of a compound claimed in any of above claims 1 to 7 and pharmaceutically acceptable carriers.

9. A method for treating a bacterial infectious diseases which comprises administering orally or parenterally an effective amount of a compound in any of above claims 1 to 7 to the patient.

* * * * *